United States Patent [19]

Tanaka et al.

[11] Patent Number: 5,686,485
[45] Date of Patent: Nov. 11, 1997

[54] PHYSIOLOGICALLY ACTIVE EI-1941 COMPOUNDS

[75] Inventors: Takeo Tanaka, Machida; Hidemasa Kondo, Shizuoka; Fumito Koizumi; Hiroki Ishiguro, both of Machida; Mayumi Yoshida, Sagamihara; Katsuhiko Ando, Machida; Yuzuru Matsuda, Koganei, all of Japan

[73] Assignee: Kyowa Hakko Kogyo Co., Ltd., Tokyo, Japan

[21] Appl. No.: 728,552

[22] Filed: Oct. 9, 1996

[30] Foreign Application Priority Data

Oct. 16, 1995 [JP] Japan ................. 7-267234
Feb. 29, 1996 [JP] Japan ................. 8-041986

[51] Int. Cl.$^6$ ................................ A61K 31/365
[52] U.S. Cl. ................ 514/454; 514/456; 549/282; 549/289; 549/387; 549/399
[58] Field of Search ................ 549/399, 289, 549/387, 282; 514/456, 454

[56] References Cited

FOREIGN PATENT DOCUMENTS

| 4 59743 | 2/1992 | Japan | 514/456 |
| 4 74121 | 3/1992 | Japan | 514/456 |
| 4202127 | 7/1992 | Japan | 514/456 |

*Primary Examiner*—James H. Reamer
*Attorney, Agent, or Firm*—Fitzpatrick, Cella, Harper & Scinto

[57] ABSTRACT

The present invention relates to EI-1941 compounds having interleukin-1 production inhibitory activity which are represented by the formula:

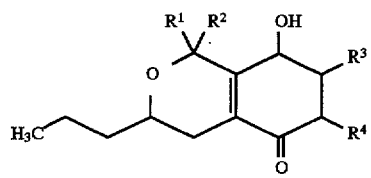

wherein either of $R^1$ and $R^2$ is hydrogen and the other is hydroxy, or $R^1$ and $R^2$ together represent oxygen; and $R^3$ is hydroxy and $R^4$ is hydrogen, or $R^3$ and $R^4$ together represent —O—.

5 Claims, No Drawings

PHYSIOLOGICALLY ACTIVE EI-1941 COMPOUNDS

BACKGROUND OF THE INVENTION

The present invention relates to novel interleukin-1β (hereinafter referred to as IL-1β) production inhibiting compounds which are produced by a microorganism belonging to the genus Farrowia. The compounds have interleukin-1 (hereinafter referred to as IL-1) production inhibitory activity and are useful for the treatment of rheumatoid arthritis, gout, osteoarthritis, osteoporosis, periarteritis nodosa, ulcerative colitis, chronic nephritis, active chronic hepatitis, septicemia, endotoxin shock, atherosclerosis, pyrexia of infectious diseases, diffuse scleroderma, and the like.

IL-1 is a protein having a molecular weight of 17.5 kDa which is produced by a variety of cells in the body such as macrophage, monocyte, neutrophil, fibroblast, skin keratinocyte, hepatic Kupffer cell, renal glomerular mesangial cell, brain astroglia, and angioendothelial cell. IL-1 includes α-form having an isoelectric point (pI) of 5 and β-form having pI of 7. At present, it is known that the α-form and the β-form exhibit the same activity.

IL-1 is known to have various biological activities. That is, IL-1 is deemed to act as a factor that enhances multiplicative division of lymphocytes and as a cofactor that enhances multiplication of B cells and production of antibodies. Further, it is considered that IL-1 acts on arachidonic acid cascade in the temperature center of the hypothalamus to increase the synthesis of prostaglandin $E_2$, thereby causing pyrexia. Furthermore, it is shown that the activity of IL-1 is significantly increased in the serum of patients suffering from septicemia or Crohn's disease and in the cavum articulare of patients who suffer from articular rheumatism. This suggests the participation of IL-1 in the attack and progress of these diseases. Suppression of the production of IL-1 is considered to be effective for alleviating the symptoms that occur through IL-1.

Examples of known compounds having IL-1 production inhibitory activity are synthetic compounds such as naphthalene derivatives (Japanese Published Unexamined Patent Application No. 59743/92), 3-arylisothiazole derivatives (Japanese Published Unexamined Patent Application No. 74121/92), and zingerol derivatives (Japanese Published Unexamined Patent Application No. 202127/92).

An object of the present invention is to provide novel physiologically active substances which have potent IL-1 production inhibitory activity.

SUMMARY OF THE INVENTION

The present invention provides EI-1941 compounds having IL-1 production inhibitory activity which are represented by formula (I):

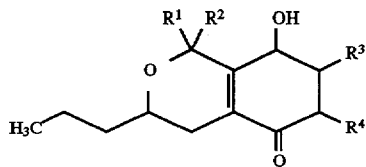

wherein either of $R^1$ and $R^2$ is hydrogen and the other is hydroxyl group, or $R^1$ and $R^2$ together represent oxygen; and $R^3$ is hydroxyl group and $R^4$ is hydrogen, or $R^3$ and $R^4$ together represent —O—.

EI-1941 compounds can be produced by culturing a microorganism belonging to the genus Farrowia.

DETAILED DESCRIPTION OF THE INVENTION

EI-1941 compounds include the compound represented by formula (I) wherein $R^1$ is hydrogen, $R^2$ is hydroxyl group, and $R^3$ and $R^4$ together represent —O— (hereinafter referred to as EI-1941-1); the compound represented by formula (I) wherein $R^1$ and $R^2$ together represent oxygen, and $R^3$ and $R^4$ together represent —O— (hereinafter referred to as EI-1941-2); and the compound represented by formula (I) wherein $R^1$ and $R^2$ together represent oxygen, $R^3$ is hydroxyl group, and $R^4$ is hydrogen (hereinafter referred to as EI-1941-3).

The physicochemical properties of EI-1941 compounds are shown below.

The data were obtained by using the following instruments.

Mass spectrum: JEOL LTD., JMS-HX/HX110A Mass spectrometer

UV absorption spectrum: Shimadzu Corporation, UV-2200 Spectrophotometer

IR absorption spectrum: JEOL LTD., JIR-RFX3001 Infrared spectrophotometer

NMR spectrum: JEOL LTD., α400 Nuclear magnetic resonance

Bruker, AM500 Nuclear magnetic resonance

Optical rotation: Nippon Bunko Kogyo Co., Ltd., DIP-370 Digital polarimeter

PHYSICOCHEMICAL PROPERTIES OF EI-1941-1

Color and form of the substance:
Brown oily substance
Specific rotation:
$[\alpha]_D^{26} = -193.7°$ (c=0.314, $CH_3OH$)
FAB MS spectrum:
m/z amu 241 $(M+H)^+$
High resolution FAB MS spectrum:
m/z amu 241.1058 $(M+H)^+$, Δ−1.8 mmu
UV absorption spectrum ($CH_3OH$):
$\lambda_{max}$ nm(ε); 209 (6,800), 241 (5,500)
+HCl unchanged
+NaOH 218, 242, 341
IR absorption spectrum (KBr):
$\nu_{max}$ nm $(cm^{-1})$; 725, 874, 1026, 1281, 1456, 1682, 2873, 2933, 2960, 3419
CD absorption spectrum ($CH_3OH$):
$\lambda_{max}$ nm(Δε); 335 (−3.0), 246 (−9.2)
$^1$H-NMR spectrum:
δ ppm (integration, multiplicity, coupling constant); 5.584 (1 H, s), 4.647 (1 H, m), 3.918 (1 H, m), 3.757 (1 H, dd, J=3.7, 1.5 Hz), 3.444 (1 H, dd, J=3.7, 1.2 Hz), 2.111 (1 H, m), 2.004 (1 H, m), 1.5 (4 H, m), 0.947 (3 H, t, J=7.2 Hz )
$^{13}$C-NMR spectrum:
δ ppm (multiplicity); 195.6 (s), 149.2 (s), 130.2 (s), 88.8 (d), 66.8 (d), 63.3 (d), 58.2 (d), 53.7 (d), 38.5 (t), 28.9 (d), 19.5 (t), 14.3 (q)
Solubility:
Readily soluble in methanol and acetonitrile
Color reaction:
Positive to the iodine test and the sulfuric acid test
Thin layer chromatography:
Rf value; 0.43
Developing solvent; chloroform-methanol (9:1 v/v)
Thin layer; HPTLC Fertigplatten Kieselgel 60 F254 (Merck & Co., Inc. )

Development; room temperature, ascending method, 20–40 minutes

Detection; coloration with iodine

PHYSICOCHEMICAL PROPERTIES OF EI-1941-2

Color and form of the substance:
 Red oily substance
FAB MS spectrum:
 m/z amu 239 (M+H)$^+$
High resolution FAB MS spectrum:
 m/z amu 239.0928 (M+H)$^+$, Δ0.9 mmu
$^1$H-NMR spectrum:
 δppm (integration, multiplicity, coupling constant); 4.946 (1 H, m), 4.5 (1 H, m), 3.838 (1 H, dd, J=3.7, 1.7 Hz), 3.553 (1 H, dd, J=3.7, 1.0 Hz), 2.535 (1 H, ddd, J=18.1, 4.7, 1.3 Hz), 2.462 (1 H, ddd, J=18.6, 10.0, 1.0 Hz), 1.6 (2 H, m), 1.4 (2 H, m), 0.922 (3 H, t, J=7.3 Hz)
$^{13}$C-NMR spectrum:
 δ ppm (multiplicity); 195.4 (s), 165.2 (s), 141.5 (s), 138.7 (d), 78.5 (d), 62.0 (d), 57.3 (d), 53.3 (d), 37.1 (t), 26.8 (t), 18.8 (t), 14.0 (q)
Solubility:
 Readily soluble in methanol and acetonitrile
Color reaction:
 Positive to the iodine test and the sulfuric acid test
Thin layer chromatography:
 Rf value; 0.68
 Developing solvent; chloroform-methanol ( 9:1 v/v)
 Thin layer; HPTLC Fertigplatten Kieselgel 60 F254 (Merck & Co., Inc.)
 Development; room temperature, ascending method, 20–40 minutes
 Detection; coloration with iodine

PHYSICOCHEMICAL PROPERTIES OF EI-1941-3

Color and form of the substance:
 Red oily substance
Specific rotation:
 $[\alpha]_D^{23}$=−87.5° (c=0.314, CH$_3$OH)
FAB MS spectrum:
 m/z amu 241 (M+H)$^+$
High resolution FAB MS spectrum:
 m/z amu 241.1061 (M+H)$^+$, Δ−1.5 mmu
UV absorption spectrum (CH$_3$OH):
 $\lambda_{max}$ nm(ε); 232 (6,800)
 +HCl unchanged
 +NaOH 214, 235, 383
IR absorption spectrum (KBr):
 $v_{max}$ nm (cm$^{-1}$); 1024, 1230, 1410, 1693, 1716, 2873, 2933, 2960, 3419
$^1$H-NMR spectrum:
 δ ppm (integration, multiplicity, coupling constant); 4.5 (1 H, m), 4.218 (1 H, q, J=3.4 Hz), 2.924 (1 H, dd, J=16.4, 3.1 Hz), 2.758 (1 H, ddd, J=18.3, 3.8, 1.3 Hz), 2.506 (1 H, dd, J=16.7, 3.8 Hz), 2.250 (1 H, ddd, J=19.4, 12.0, 2.3 Hz), 1.7 (2 H, m), 1.5 (2 H, m), 0.941 (3 H, t, J=7.3 Hz )
$^{13}$C-NMR spectrum:
 δ ppm (multiplicity); 197.7 (s), 167.0 (s), 143.5 (s), 136.2 (s), 79.0 (d), 70.4 (d), 66.6 (d), 41.6 (t), 37.7 (t), 26.3 (t), 18.8 (t), 14.0 (q)
Solubility:
 Readily soluble in methanol and acetonitrile
Color reaction:
 Positive to the iodine test and the sulfuric acid test Thin layer chromatography:
 Rf value; 0.41
 Developing solvent; chloroform-methanol ( 9:1 v/v)
 Thin layer; HPTLC Fertigplatten Kieselgel 60 F254 (Merck & Co., Inc. )
 Development; room temperature, ascending method, 20–40 minutes
 Detection; coloration with iodine The activity of EI-1941 compounds is described below by Test Example.

TEST EXAMPLE

Inhibitory Activity Against the Production of IL-1

The inhibitory activity of EI-1941 compounds against the production of IL-1β by human monocyte-derived THP-1 cells (ATCC No. TIB 202) was examined in the following manner. The amount of IL-1β was determined by the ELISA method.

THP-1 cells were suspended in RPMI1640 medium (Nissui Pharmaceutical Co., Ltd.) containing 10% inactivated fetal calf serum at a concentration of 1×10$^5$ cells/ml. The cell suspension was put into wells of a 24-well plate in an amount of 1 ml/well. Phorbol 12-myristate 13-acetate (PMA, final concentration: 30 nM) was added to the wells, followed by incubation in a 5% CO$_2$-incubator at 37° C. for 65 hours to differentiate the cells into macrophage.

Then, the plate was gently washed with serum-free RPMI1640 medium to remove the cells which were not adhered to the wells, and the residue was cultured for 4 hours in serum-free RPMI1640 medium (1 ml/well) containing lipopolysaccharide (LPS, final concentration: 25 μg/ml) and a test compound (final concentration: 0.05–50 μg/ml).

After the completion of culturing, the amount of IL-1β released into the culture supernatant was determined by using an IL-1β determination kit (Amersham Corp.).

The IL-1 production inhibition rate was calculated according to the following equation to obtain IC$_{50}$ (50% inhibitory concentration).

IL-1 production inhibition rate (%)=(A−B)/(A−C)×100
 A: Amount of IL-1 produced when only LPS is added
 B: Amount of IL-1 produced when LPS and test compound are added
 C: Amount of IL-1 produced when LPS is not added The result is shown in Table 1.

TABLE 1

| Compound | IC$_{50}$ (μM) |
|---|---|
| EI-1941-1 | 1 |
| EI-1941-2 | 2.2 |
| EI-1941-3 | >50 |

The process for producing EI-1941 compounds is described below.

EI-1941 compounds can be obtained by culturing in a medium a microorganism belonging to the genus Farrowia and having the ability to produce EI-1941 compounds, allowing EI-1941 compounds to accumulate in the culture, and recovering EI-1941 compounds from the culture.

As the EI-1941-compound-producing strains of the present invention, any strains which belong to the genus Farrowia and have the ability to produce EI-1941 compounds can be used. In addition, any mutants of such strains which are obtained by various artificial mutation methods such as UV irradiation, X ray irradiation and treatment with mutagens or by spontaneous mutation may also be used in the present invention, insofar as they have the ability to produce EI-1941 compounds. A typical example of a suitable strain is *Farrowia sp.* E-1941 strain.

The mycological properties of *Farrowia sp.* E-1941 strain are described below.

1. Macroscopic Observation

When the strain is cultured at 25° C. on malt extract agar media, the diameter of a colony reaches 43–46 mm on the seventh day of culturing. On the fourteenth day, the color of the colony is mustard brown and is beige at the periphery; and the color of the reverse side is oatmeal and is slate tan at the center.

When the strain is cultured at 25° C. on potato-glucose agar media, the diameter of a colony reaches 50–56 mm on the seventh day of culturing. On the fourteenth day, the color of the colony is covert brown and is covert tan at the periphery; and the color of the reverse side is light mustard tan and is deep brown at the center.

The growth temperature range for this strain is 12°–34.5° C. and the optimum growth temperature is about 26° C. The pH range which allows its growth is 2–11 and the optimum growth pH is around 8.

2. Optical Microscopic Observation of the Strain when Cultured on a Potato-Glucose Agar Medium Hyphae are septate and branch well. Many perithecia are formed on the medium. The perithecium is small lageniform and its color is brown to dark brown. It is 126–274 μm long and 53–116 μm wide and has a short conical ostiole at the tip. Setae are slightly formed on the perithecium as terminal hair and lateral hair, which are difficult to distinguish from each other. The seta is light brown to brown, straight without branching, and septate. It is 85–205 μm long and 4–5.5 μm wide at the base and tapers. Asci are formed within the perithecium and are colorless, smooth and clavate. The ascus is unitunicate, rapidly deliquescing and eight-spored. The ascospore is olive brown, smooth and unicellular, and has an unclear germ pore. The shape of ascospore is wide ellipsoidal or limoniform with both ends being slightly pointed. The ascospore is 8–10 μm long and 6–9.5 μm wide and is released from the ostiole at the tip of perithecium.

On the basis of the above mycological properties, the strain is classified in the genus Farrowia. Strains of the genus Farrowia are described in detail in "Farrowia, a new genus in the Chaetomiaceae," Persoonia, Vol. 8, No. 2, p. 167 (1975) by D. L. Hawksworth.

The strain was named *Farrowia sp.* E-1941 and was deposited with the National Institute of Bioscience and Human-Technology, Agency of Industrial Science and Technology on Oct. 6, 1995 with accession number FERM BP-5258.

For the culturing of the EI-1941-compound-producing strains used in the present invention, conventional methods for culturing filamentous fungi are generally employed. As the medium, either a synthetic medium or a natural medium may be used insofar as it appropriately contains carbon sources, nitrogen sources, inorganic substances, and the like which can be assimilated by the strains employed.

Examples of the carbon sources include carbohydrates such as glucose, fructose, sucrose, stabilose, starch, dextrin, mannose, maltose and molasses; organic acids such as citric acid, malic acid, acetic acid and fumaric acid; alcohols such as methanol and ethanol; hydrocarbons such as methane, ethane, propane and n-paraffins; amino acids such as glutamic acid; and glycerol.

Examples of the nitrogen sources include ammonium salts such as ammonium chloride, ammonium sulfate, ammonium nitrate and ammonium phosphate, amino acids such as aspartic acid, glutamine, cystine and alanine, urea, peptone, meat extract, yeast extract, dry yeast, corn steep liquor, soybean powder, cottonseed cake, soybean casein, casamino acid and Pharmamedia.

Examples of the inorganic substances include potassium monohydrogenphosphate, potassium dihydrogenphosphate, sodium dihydrogenphosphate, magnesium sulfate, ferrous sulfate, manganese sulfate, copper sulfate, cobalt sulfate, zinc sulfate, calcium pantothenate, ammonium molybdate, potassium aluminum sulfate, barium carbonate, calcium carbonate, cobalt chloride and sodium chloride.

If necessary, substances that promote the growth of cells or the production of EI-1941 compounds such as vitamins (e.g. thiamine) may be added to the medium. If the strain employed requires specific substances, such substances are also added to the medium.

Culturing is carried out by Shaking culture, aeration stirring culture, or the like at 20°–40° C. and at pH around neutrality. Usually, by culturing for 3–7 days, the amount of EI-1941 compounds accumulated in the culture reaches maximum, and the culturing is completed.

For the isolation and purification of EI-1941 compounds from the culture, an ordinary method for isolating a microbial metabolite from the culture can be utilized.

That is, EI-1941 compounds can be isolated and purified by extraction of microbial cells with a solvent such as acetone or methanol, removal of microbial cells by filtration or centrifugation, adsorption and desorption of an active substance by column chromatography or thin layer chromatography using an adsorption resin, silica gel, silanised silica gel, reversed-phase silica gel, aluminum, cellulose, diatomaceous earth, magnesium silicate, gel filter medium, an ion exchange resin, etc., partition with a suitable solvent, and the like.

During the above isolation and purification steps, EI-1941 compounds can be traced by silica gel thin layer chromatography and then by iodine color development or ultraviolet irradiation at 253.6 nm.

EI-1941 compounds which are used as IL-1 production inhibitors can be administered as such or as pharmaceutical compositions either orally or parenterally. The forms of pharmaceutical compositions include tablets, pills, powders, granules, capsules, suppositories, injections and eye drops.

These pharmaceutical compositions can be prepared by generally known methods. For example, the compositions may be formulated to contain various excipients, lubricants, binders, disintegrators, suspending agents, isotonizing agents, emulsifying agents, absorption accelerators, and the like.

Examples of the carriers to be used in the pharmaceutical compositions are water, distilled water for injection, physiological saline, glucose, fructose, sucrose, mannitol, lactose, starch, corn starch, potato starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters. These carriers are appropriately selected depending on the preparation form.

The dose will vary depending on the desired therapeutic effect, the mode of administration, the administration period, the age and weight of a patient, etc.

Certain embodiments of the invention are illustrated in the following Example.

EXAMPLE 1

*Farrowia sp.* E-1941 strain was used as the seed strain.

One loopful of the strain was inoculated into 10 ml of a first medium (pH 6.5) comprising 100 g/l glucose, 30 g/l mashed potatoes (Snow Brand Milk Products Co., Ltd.) and 5 g/l powdery yeast extract S (Nippon Seiyaku Co., Ltd.) in each of three 50-ml test tubes (total amount of the medium: 30 ml). Culturing was carried out with shaking at 25° C. for 4 days.

The resulting first culture (30 ml) was inoculated in 5 ml portions into six 300-ml Erlenmeyer flasks each containing 50 ml of a second medium (total amount of the medium: 300 ml). The composition of the second medium was the same as that of the first medium. Culturing was carried out with shaking at 25° C. for 2 days.

The resulting second culture (300 ml) was inoculated in 50 ml portions into six 2-l Erlenmeyer flasks each containing 500 ml of a third medium (total amount of the medium: 3 l). The composition of the third medium was the same as that of the second medium. Culturing was carried out with shaking at 28° C. for 2 days.

The resulting third culture (3 l) was inoculated in 1.5 l portions into two 30-l stainless steel jar fermentors each containing 16.5 l of a main fermentation medium (total amount of the culture: 36 l). The composition of the main fermentation medium was as follows: 20 g/l glucose, 20 g/l mashed potatoes, 5 g/l peptone (Kyokuto Seiyaku Co., Ltd.), 5 g/l $KH_2PO_4$, and 0.5 g/l $Mg_3(PO_4)_2 \cdot 8H_2O$ (pH 6.0). Culturing was carried out at 25° C. with stirring and aeration (rotation: 250 rpm, aeration: 18 l/min.) for 5 days.

The resulting culture (36 l) was centrifuged (H-130E centrifuge, Kokusan Chemical Works Co., Ltd.) and the obtained supernatant was passed through a Diaion HP-20 column (2 l, Mitsubishi Chemical Corporation). After washing with 8 l of water, 8 l of 20% methanol and 8 l of 40% methanol, elution was carried out with 8 l of methanol-acetone (7:3 v/v). The fractions containing EI-1941 compounds were combined and 100 g of Radiolite #600 (Showa Kagaku Kogyo Co., Ltd.) was added thereto, followed by concentration to dryness under reduced pressure. The concentrate was applied to a silica gel column (2 l, Art. 7734, Merck & Co., Inc.) and eluted with 8 l of chloroform, 8 l of chloroform-methanol (99:1 v/v) and then 8 l of chloroform-methanol (97:3 v/v). The EI-1941-1-containing fractions and the EI-1941-2-containing fractions were respectively combined and concentrated to dryness under reduced pressure. The EI-1941-1-containing concentrate was dissolved in 50 ml of methanol and the EI-1941-2-containing concentrate was dissolved in 85 ml of methanol to give a crude EI-1941-1 solution and a crude EI-1941-2 solution.

The crude EI-1941-1 solution was divided into small portions (2 ml each), and one portion was passed through HPLC column (D-ODS-5-B S-5 120A, YMC). Elution was carried out with 25% acetonitrile at a flow rate of 20 ml/min, and the EI-1941-1-containing fractions were combined. After purification of the other portions by repeated HPLC, the EI-1941-1-containing fractions were combined and concentrated to dryness under reduced pressure to give 200 mg of EI-1941-1.

The crude EI-1941-2 solution was divided into small portions (2 ml each), and one portion was passed through HPLC column (D-ODS-5-B S-5 120A, YMC). Elution was carried out with 30% acetonitrile at a flow rate of 20 ml/min, and the EI-1941-2-containing fractions were combined. After purification of the other portions by repeated HPLC, the EI-1941-2-containing fractions were combined and concentrated to dryness under reduced pressure to give 100 mg of EI-1941-2.

EI-1941-3 is prepared from EI-1941-2 stored at room temperature in the dry state. EI-1941-2 (80 mg) which had been stored was dissolved in 4 ml of methanol. The solution was divided into two portions (2 ml each) and each portion was passed through HPLC column (D-ODS-5-B S-5 120A, YMC). Elution was carried out with 30% acetonitrile at a flow rate of 20 ml/min to separate EI-1941-2-containing fractions and EI-1941-3-containing fractions. The EI-1941-3-containing fractions were combined and concentrated to dryness under reduced pressure to give 13 mg of EI-1941-3.

During the above steps, EI-1941 compounds were traced by silica gel thin layer chromatography and then by iodine color development or ultraviolet irradiation at 253.6 nm.

What is claimed is:

1. EI-1941 compounds which are represented by formula (I):

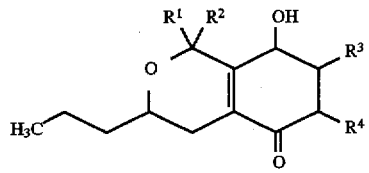

wherein either of $R^1$ and $R^2$ is hydrogen and the other is hydroxy, or $R^1$ and $R^2$ together represent oxygen; and $R^3$ is hydroxy and $R^4$ is hydrogen, or $R^3$ and $R^4$ together represent —O—.

2. A compound according to claim 1, wherein $R^1$ is hydrogen, $R^2$ is hydroxy, and $R^3$ and $R^4$ together represent —O—.

3. A compound according to claim 1, wherein $R^1$ and $R^2$ together represent oxygen, and $R^3$ and $R^4$ together represent —O—.

4. A compound according to claim 1, wherein $R^1$ and $R^2$ together represent oxygen, $R^3$ is hydroxy, and $R^4$ is hydrogen.

5. A pharmaceutical composition comprising a pharmaceutically acceptable carrier and as an active ingredient, an effective amount of a compound as defined by claim 1.

* * * * *